(12) United States Patent
Kitagawa et al.

(10) Patent No.: US 7,745,661 B2
(45) Date of Patent: Jun. 29, 2010

(54) PROCESS FOR PRODUCING TRICARBOXYLIC ACID TRIS (ALKYL-SUBSTITUTED CYCLOHEXYLAMIDE)

(75) Inventors: Sachio Kitagawa, Kyoto (JP); Masahide Ishikawa, Kyoto (JP); Yoshihiro Ishibashi, Kyoto (JP); Taiichiro Iwamura, Kyoto (JP); Yoshihiro Kihara, Kyoto (JP)

(73) Assignee: New Japan Chemical Co., Ltd., Kyoto-shi (JP)

( * ) Notice: Subject to any disclaimer, the term of this patent is extended or adjusted under 35 U.S.C. 154(b) by 496 days.

(21) Appl. No.: 11/911,054

(22) PCT Filed: Apr. 5, 2006

(86) PCT No.: PCT/JP2006/307246

§ 371 (c)(1),
(2), (4) Date: Oct. 9, 2007

(87) PCT Pub. No.: WO2006/109654

PCT Pub. Date: Oct. 19, 2006

(65) Prior Publication Data

US 2009/0069599 A1    Mar. 12, 2009

(30) Foreign Application Priority Data

Apr. 7, 2005    (JP) .............................. 2005-111256

(51) Int. Cl.
C07C 231/02    (2006.01)
(52) U.S. Cl. ...................................... 564/138; 564/139
(58) Field of Classification Search ................ 564/138, 564/139
See application file for complete search history.

(56) References Cited

U.S. PATENT DOCUMENTS 6,335,468 B1    1/2002    Hatajima et al.

FOREIGN PATENT DOCUMENTS

| EP | 0 776 933 A1 | 6/1997 |
|---|---|---|
| EP | 1 094 059 A1 | 4/2001 |
| JP | 61-000050 A | 1/1986 |
| JP | 06-192496 | 7/1994 |
| JP | 7-242610 A | 9/1995 |
| JP | 07-309821 A | 11/1995 |
| JP | 2001-187769 A | 7/2001 |
| JP | 2002-265472 A | 9/2002 |
| WO | WO 00/52089 A1 | 9/2000 |
| WO | 02/46300 A2 | 6/2002 |

OTHER PUBLICATIONS

Tang, Pingwah; "Boric Acid Catalyzed Amide Formation From Carboxylic Acids and Amines: N-Benzyl-4-Phenylbutyramide"; Organic Synthesis, 2005, pp. 262-267, vol. 81, (XP-002519978).
Ishihara, K.; "(3,4,5-Trifluorophenyl) Boronic Acid-Catalyzed Amide Formation From Carboxylic Acids and Amines: N-Benzyl-4-Phenylbutyramide"; Organic Syntheses, 2004, pp. 176-182, vol. 79, (XP-002519979).
European Search Report dated Apr. 2, 2009, issued in corresponding European Patent Application No. 06731194.4.
Ishihara, K.; "(3,4,5-Trifluorophenyl) Boronic Acid-Catalyzed Amide Formation From Carboxylic Acids and Amines: N-Benzyl-4-Phenylbutyramide"; Organic Syntheses, 2002, pp. 176-182, vol. 79, (XP-002519979).
International Search Report of PCT/JP2006/307246, date of mailing Jun. 6, 2006.

*Primary Examiner*—Shailendra Kumar
(74) *Attorney, Agent, or Firm*—Westerman, Hattori, Daniels & Adrian, LLP

(57)    ABSTRACT

Disclosed are, for example, a process for producing a tricarboxylic acid tris(alkyl-substituted cyclohexylamide), the process comprising subjecting a tricarboxylic acid and an alkyl-substituted cyclohexylamine to an amidation reaction, either (a) in the presence of a boric acid compound and a phenol compound or (b) in the presence of a boric acid ester obtained by the dehydration condensation of a boric acid compound and a phenol compound, and optionally purifying the resulting crude reaction product.

13 Claims, No Drawings

PROCESS FOR PRODUCING TRICARBOXYLIC ACID TRIS (ALKYL-SUBSTITUTED CYCLOHEXYLAMIDE)

This application is a 371 of PCT/JP2006/307246, filed Apr. 5, 2006.

TECHNICAL FIELD

The present invention relates to a novel process for producing a tricarboxylic acid tris(alkyl-substituted cyclohexylamide), and more particularly relates to a process for producing a tricarboxylic acid tris(alkyl-substituted cyclohexylamide) by an amidation reaction of a tricarboxylic acid and an alkyl-substituted cyclohexylamine.

BACKGROUND ART

Because of their excellent moldability, mechanical properties, electrical properties, and so forth, polyolefin resins are used in many different fields as materials for film molding, sheet molding, blow molding, injection molding, and so on.

However, while these resins generally do have excellent properties, they are less than satisfactory in terms of transparency, crystallinity, and rigidity, and in some applications the excellent performance inherent in such resins cannot be fully taken advantage of, and at present this limits the applications of these resins. A technique in which an amide compound is employed has been proposed in the past in an effort to improve the transparency, crystallinity, and rigidity of polyolefin resins (see Patent Documents 1-3).

A number of processes have been disclosed up to now for producing a 1,2,3-propanetricarboxylic acid tris(alkyl-substituted cyclohexylamide) as the above-mentioned amide compound.

For example, Japanese Laid-Open Patent Application H7-242610 (Patent Document 2) gives a preparation example in which 1,2,3-propanetricarboxylic acid tris(cyclohexylamide) and 1,2,3-propanetricarboxylic acid tris(2-methylcyclohexylamide) are obtained by reacting 1,2,3-propanetricarboxylic acid and cyclohexylamine or 2-methylcyclohexylamine in the presence of both triphenyl phosphite and pyridine.

However, the triphenyl phosphite used in this process as an activator of carboxyl groups is extremely expensive, and furthermore, it has to be used in a large quantity, that is, in a stoichiometric amount, and this drives up the cost. Moreover, phosphorous-containing waste liquid is produced, and this necessitates treatment for environmental safety.

In addition, a preparation is given in which 1,2,3-propanetricarboxylic acid trimethyl ester and cyclohexylamine or 2-methylcyclohexylamine used in an amount corresponding to 3 to 30 equivalents thereof are subjected to an ester-amide interchange reaction for 6 hours at 220° C. to obtain a corresponding 1,2,3-propanetricarboxylic acid tris(alkyl-substituted cyclohexylamide) (see Patent Document 4).

However, this process entails a complicated step of producing a methyl ester of 1,2,3-propanetricarboxylic acid, and furthermore the reaction is conducted at a temperature not lower than the boiling point of cyclohexylamine, which means that a costly pressure-resistant equipment is required, and for this and other reasons this process has room for improvement in terms of producing and cost.

Thus, a problem has been that a 1,2,3-propanetricarboxylic acid tris(alkyl-substituted cyclohexylamide) having the specific structure of the present invention cannot always be produced easily and with good productivity with conventional production processes.

Meanwhile, it has been disclosed concerning amidation reaction that in an amidation reaction of N-acylamino acid and a primary amine, secondary amine or ammonia, a boric acid compound effectively serves as a dehydration condensation reaction catalyst, particularly in the presence of an aliphatic alcohol that serves as an auxiliary solvent (see Patent Document 5 and Patent Document 6). Boric acid compounds are inexpensive and readily available. Nevertheless, these publications include neither reference to nor implication of an amidation reaction between a tricarboxylic acid and an alkyl-substituted cyclohexylamine.

Patent Document 1: Japanese Patent No. 3401868

Patent Document 2: Japanese Laid-Open Patent Application H7-242610

Patent Document 3: International Laid-Open Patent Application pamphlet WO/00/52089

Patent Document 4: Japanese Laid-Open Patent Application H7-309821

Patent Document 5: Japanese Laid-Open Patent Application S61-000050

Patent Document 6: Japanese Laid-Open Patent Application 2001-187769

DISCLOSURE OF THE INVENTION

Problems to be Solved by the Invention

It is an object of the present invention to provide a simple process for producing a tricarboxylic acid tris(alkyl-substituted cyclohexylamide) that solves the problems of production, cost, and so forth encountered with conventional processes for producing tricarboxylic acid tris(alkyl-substituted cyclohexylamides).

Means for Solving the Problem

In light of this situation, the inventors conducted diligent study aimed at solving the above problems, and as a result learned the following.

(a) If diboron trioxide, which is inexpensive and readily available, is used in an amidation reaction of 1,2,3-propanetricarboxylic acid and 2-methylcyclohexylamine, tricarboxylic acid tris(2-methylcyclohexylamide) is obtained, but the yield is extremely low, being about 20% at best.

The cause of this low yield was examined, which revealed that the production of by-products having an imide ring structure is predominant. For example, in the case of an amidation reaction of 1,2,3-propanetricarboxylic acid and an alkyl-substituted cyclohexylamine, a by-product (hereinafter referred to as an "amide-imide") results that is represented by the following General Formula (4):

[Chemical formula 1]

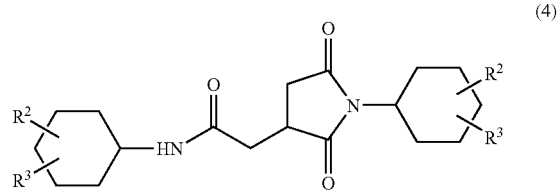

wherein $R^2$ and $R^3$ have the same meaning as $R^2$ and $R^3$ in General Formula (2) below. It was found that to solve this problem of low yield and selectively obtain the desired tricarboxylic acid tris(alkyl-substituted cyclohexylamide) at a high yield, it is important to suppress this side reaction somehow.

(b) In view of this, the inventors subjected a tricarboxylic acid and an alkyl-substituted cyclohexylamine to an amidation reaction using diboron trioxide as a boric acid compound and 2-ethylhexanol as an aliphatic alcohol according to the process discussed in the above-mentioned Japanese Laid-Open Patent Application 2001-187769, whereupon the desired tricarboxylic acid tris(alkyl-substituted cyclohexylamide) was only obtained in a far lower yield (approximately 2%) than when diboron trioxide was used alone.

It was therefore revealed that with this process it would be very difficult to obtain the desired tricarboxylic acid tris(alkyl-substituted cyclohexylamide) at a high yield. Accordingly, the inventors presumed that it was impossible to obtain the desired tricarboxylic acid tris(alkyl-substituted cyclohexylamide) at a yield over 20% when a boric acid compound is used.

(c) However, follow-up research by the inventors led to the surprising discovery that if diboron trioxide and a phenol compound are used, or if a boric acid ester obtained by the dehydration condensation of diboron trioxide and a phenol compound is used, as a dehydration condensation reaction catalyst in an amidation reaction of a tricarboxylic acid and an alkyl-substituted cyclohexylamine, a tricarboxylic acid tris(alkyl-substituted cyclohexylamide) can be produced more simply than in the past, and furthermore the formation of by-products is suppressed, the desired product is easy to purify, and the yield, purity, etc. of the desired product are satisfactory. The inventors also discovered that similar effect is obtained when another boric acid compound is used instead of diboron trioxide.

(d) Furthermore, it was found that the crude desired product thus obtained contains as impurities the amide-imide represented by the above-mentioned General Formula (4), the boric acid compound and phenol compound, or the boric acid ester of a phenol compound, used as a catalyst, mono-, di-, or triamine salts (hereinafter referred to as "amine salts") that are amidation reaction intermediates of a tricarboxylic acid and an alkyl-substituted cyclohexylamine, and so forth, but that these impurities can be easily removed by a process that is extremely advantageous in an industrial setting, namely, by just washing with a solvent.

The present invention was perfected as a result of further research based on the above findings, and provides a process for producing the tricarboxylic acid tris(alkyl-substituted cyclohexylamide), and a process for producing a purified tricarboxylic acid tris(alkyl-substituted cyclohexylamide) as mentioned below.

Item 1. A process for producing a tricarboxylic acid tris(alkyl-substituted cyclohexylamide) represented by General Formula (3):

[Chemical formula 2]

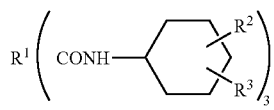

(3)

wherein $R^1$ is a $C_3$ to $C_{10}$ trivalent saturated aliphatic hydrocarbon group, a $C_5$ to $C_{15}$ trivalent saturated alicyclic hydrocarbon group, or a $C_6$ to $C_{15}$ trivalent aromatic hydrocarbon group, and $R^2$ and $R^3$ are the same or different and are each a hydrogen atom or a $C_1$ to $C_4$ linear or branched alkyl group, the process comprising subjecting a tricarboxylic acid represented by the following General Formula (1):

[Chemical formula 3]

(1)

wherein $R^1$ has the same meaning as $R^1$ in General Formula (3) and an alkyl-substituted cyclohexylamine represented by the following General Formula (2):

[Chemical formula 4]

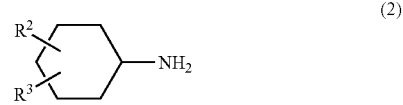

(2)

wherein $R^2$ and $R^3$ has the same meaning as $R^2$ and $R^3$ in General Formula (3) to an amidation reaction (a) in the presence of a boric acid compound and a phenol compound, or (b) in the presence of a boric acid ester obtained by the dehydration condensation of a boric acid compound and a phenol compound, to obtain a crude tricarboxylic acid tris(alkyl-substituted cyclohexylamide).

Item 2. The process according to Item 1 above, wherein the boric acid compound is at least one member selected from the group consisting of orthoboric acid, metaboric acid, pyroboric acid, tetraboric acid, and diboron trioxide.

Item 3. The process according to Item 1 or Item 2 above, wherein the phenol compound is phenol or cresol (that is, o-, m- or p-cresol or a mixture of these isomers).

Item 4. The process according to Item 1 above, wherein the boric acid ester is a boric acid ester formed from phenol or cresol and at least one boric acid compound selected from the group consisting of orthoboric acid, metaboric acid, pyroboric acid, tetraboric acid and diboron trioxide.

Item 5. The process according to any one of Items 1 to 4 above, wherein the amidation reaction is conducted at a reaction temperature of 98 to 180° C.

Item 6. The process according to any one of Items 1 to 5 above, wherein the amidation reaction is conducted in the presence of an azeotropic dehydration solvent.

Item 7. The process according to Item 6 above, wherein the azeotropic dehydration solvent is a saturated aliphatic hydrocarbon, a saturated alicyclic hydrocarbon, an aromatic hydrocarbon, or a mixture of these.

Item 8. The process according to Item 7 above, wherein the azeotropic dehydration solvent has a boiling point of 120 to 160° C.

In the specification and claims, "the boiling point" indicates a boiling point under 1 atm unless otherwise noted.

Item 9. The process according to any one of Items 1 to 8 above, wherein the tricarboxylic acid tris(alkyl-substituted cyclohexylamide) is 1,2,3-propanetricarboxylic acid tris(cyclohexylamide), 1,2,3-propanetricarboxylic acid tris(2-methylcyclohexylamide), trimesic acid tris(cyclohexylamide), trimesic acid tris(2-methylcyclohexylamide), 1,3,5-cyclohexanetricarboxylic acid tris(cyclohexylamide), or 1,3,5-cyclohexanetricarboxylic acid tris(2-methylcyclohexylamide).

Item 10. The process according to Item 9 above, wherein the tricarboxylic acid tris(alkyl-substituted cyclohexylamide) is 1,2,3-propanetricarboxylic acid tris(2-methylcyclohexylamide).

Item 11. The process according to any one of Items 1 to 10 above, which further comprises the step of purifying the crude tricarboxylic acid tris(alkyl-substituted cyclohexylamide).

Item 12. The process according to Item 11 above, wherein the purification step comprises the step of washing the crude tricarboxylic acid tris(alkyl-substituted cyclohexylamide) with a $C_1$ to $C_3$ aliphatic alcohol or with a mixture of water and a $C_1$ to $C_3$ aliphatic alcohol.

Item 13. The process according to Item 11 or 12 above, wherein the purification step is conducted until the boron content in the tricarboxylic acid tris(alkyl-substituted cyclohexylamide) as measured by ICP spectrometry (inductively coupled plasma atomic emission spectrometry) reaches 100 ppm or less.

Item 14. A production process for producing a purified tricarboxylic acid tris(alkyl-substituted cyclohexylamide), comprising the step of washing a crude tricarboxylic acid tris(alkyl-substituted cyclohexylamide) with a purification solvent.

Item 15. The production process according to Item 14 above, wherein the purification solvent is a $C_1$ to $C_3$ aliphatic alcohol or a mixture of water and a $C_1$ to $C_3$ aliphatic alcohol.

Item 16. The production process according to Item 14 above, wherein impurities contained in the crude tricarboxylic acid tris(alkyl-substituted cyclohexylamide) include a compound represented by General Formula (4):

[Chemical formula 5]

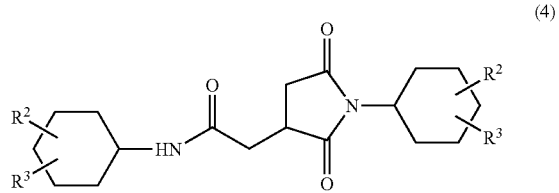

(4)

wherein $R^2$ and $R^3$ are the same or different and are each a hydrogen atom or a $C_1$ to $C_4$ linear or branched alkyl group.

Effects of the Invention

With the production process of the present invention, compared to conventional production processes, a tricarboxylic acid tris(alkyl-substituted cyclohexylamide) that is useful as a clarifying agent for a polypropylene-based resin can be obtained easily and at good productivity.

Also, with the present invention, formation of by-products is suppressed, so the desired product can be obtained with satisfactory yield, purity, and so forth.

Further, this process is industrially advantageous because purification of the desired product thus obtained is extremely simple, requiring only washing with an alcohol or a mixture of water and an alcohol.

The present invention is particularly advantageous in that the desired product can be obtained with a good hue (white color). For instance, when using propanetricarboxylic acid produced by a hydrogen peroxide oxidation reaction in the presence of a phosphorus-tungsten catalyst, the reaction solution becomes yellow to green in color, and there was an apprehension that coloring components are adsorbed to the crystals of the desired compound. When the production and purification processes of the present invention are employed, however, a product with good hue (a white solid) is obtained.

BEST MODE FOR CARRYING OUT THE INVENTION

The present invention will now be described in detail.

[Tricarboxylic Acid]

The tricarboxylic acid used in the present invention is represented by the following General Formula (1):

[Chemical formula 6]

(1)

wherein $R^1$ is a $C_3$ to $C_{10}$, and preferably $C_3$ to $C_8$, and more preferably $C_3$ to $C_6$, trivalent saturated aliphatic hydrocarbon group, a $C_5$ to $C_{15}$, and preferably $C_5$ to $C_{10}$, and more preferably $C_5$ to $C_8$, trivalent saturated alicyclic hydrocarbon group, or a $C_6$ to $C_{15}$, and preferably $C_6$ to $C_{10}$, and more preferably $C_6$ to $C_8$, trivalent aromatic hydrocarbon group. Examples of this tricarboxylic acid include saturated aliphatic tricarboxylic acids, saturated alicyclic tricarboxylic acids, and aromatic tricarboxylic acids. The tricarboxylic acids represented by General Formula (1) are either known and readily available or can be easily produced by a known process.

$R^1$ here is a trivalent organic group obtained by removing the three carboxyl groups from a tricarboxylic acid represented by General Formula (1). More specifically, $R^1$ is a residue formed by removing three carboxyl groups from a $C_6$ to $C_{13}$, and preferably $C_6$ to $C_{11}$, and more preferably $C_6$ to $C_9$, saturated aliphatic tricarboxylic acid, or a residue formed by removing three carboxyl groups from a $C_8$ to $C_{18}$, and preferably $C_8$ to $C_{13}$, and more preferably $C_8$ to $C_{11}$, saturated alicyclic tricarboxylic acid, or a residue formed by removing three carboxyl groups from a $C_9$ to $C_{18}$, and preferably $C_9$ to $C_{13}$, and more preferably $C_9$ to $C_{11}$, aromatic tricarboxylic acid.

Specific examples of saturated aliphatic tricarboxylic acids include 1,2,3-propanetricarboxylic acid, 1-methyl-1,2,3-propanetricarboxylic acid, 2-methyl-1,2,3-propanetricarboxylic acid, 1-ethyl-1,2,3-propanetricarboxylic acid, 1,2,4-butanetricarboxylic acid, 1,3,5-pentanetricarboxylic acid, 1,2,5-hexanetricarboxylic acid, etc. Of these, 1,2,3-propanetricarboxylic acid is particularly preferred. These saturated aliphatic tricarboxylic acids may be monoanhydrides in which two of the three carboxyl groups form acid anhydride group.

Specific examples of saturated alicyclic tricarboxylic acids include cyclopentanetricarboxylic acids that may be substituted with one or more saturated aliphatic groups, cyclohexanetricarboxylic acids that may be substituted with one or more saturated aliphatic groups, and decahydronaphthalenetricarboxylic acids that may be substituted with one or more saturated aliphatic groups. Examples of the above-mentioned saturated aliphatic group include $C_1$ to $C_3$ alkyl groups. When these substituents are present, the number of such substituents is 1 or 2, particularly 1. Examples of saturated alicyclic tricarboxylic acids include 1,2,4-cyclopentanetricarboxylic acid, 1,2,3-cyclohexanetricarboxylic acid, 4-methyl-1,2,3- cyclohexanetricarboxylic acid, 1,2,4-cyclohexanetricarboxylic acid, 6-methyl-1,2,4-cyclohexanetricarboxylic acid, 1,3,5-cyclohexanetricarboxylic acid, 1,2,4-decahydronaphthalenetricarboxylic acid, and 1,2,5-decahydronaphthalenetricarboxylic acid. Of these, 1,3,5-cyclohexanetricarboxylic acid is particularly preferable.

These saturated alicyclic tricarboxylic acids may be monoanhydrides in which two of the three carboxyl groups form acid anhydride groups.

Specific examples of aromatic tricarboxylic acids include trimellitic acid, trimesic acid, 1,2,3-benzenetricarboxylic acid, 1,2,4-naphthalenetricarboxylic acid, 1,2,5-naphthalenetricarboxylic acid, 1,4,5-naphthalenetricarboxylic acid, 2,3,6-naphthalenetricarboxylic acid, 1,3,6-naphthalenetricarboxylic acid, etc., and these aromatic tricarboxylic acids may be substituted with one or more saturated aliphatic group. Examples of the above-mentioned saturated aliphatic group include $C_1$ to $C_3$ alkyl groups, and more specifically methyl, ethyl, n-propyl, iso-propyl, etc. When these substituents are present, the number of such substituents is 1 or 2, particularly 1.

These aromatic tricarboxylic acids may be monoanhydrides in which two of the three carboxyl groups form acid anhydride groups. Of these, trimesic acid is particularly preferable.

Alkyl-Substituted Cyclohexylamine

In the alkyl-substituted cyclohexylamine represented by the following General Formula (2) in the present invention:

[Chemical formula 7]

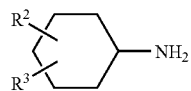

(2)

wherein $R^2$ and $R^3$ are the same or different and are each a hydrogen atom or a $C_1$ to $C_4$ linear or branched alkyl group, examples of the $C_1$ to $C_4$ linear or branched alkyl group represented by RF and $R^3$ include methyl, ethyl, propyl, iso-propyl, butyl, isobutyl, sec-butyl, and tert-butyl. Of these, $C_1$ to $C_3$ alkyl groups, particularly methyl, ethyl, n-propyl and i-propyl, are preferable.

It is also preferable that one of $R^2$ and $R^3$ is a hydrogen atom, and the other is a $C_1$ to $C_4$ alkyl group, particularly methyl, ethyl, n-propyl or i-propyl. In this case there are no particular restrictions on the substitution position of the alkyl group, but the 2- or 4-position with respect to the amino group is preferable.

It is also preferable that $R^2$ and $R^3$ both represent a hydrogen atom.

These alkyl-substituted cyclohexylamines represented by General Formula (2) are either known and readily available or can be easily produced by a known process.

Specific examples of the alkyl-substituted cyclohexylamines represented by General Formula (2) include cyclohexylamine, 2-methylcyclohexylamine, 3-methylcyclohexylamine, 4-methylcyclohexylamine, 2-ethylcyclohexylamine, 3-ethylcyclohexylamine, 4-ethylcyclohexylamine, 2-n-propylcyclohexyl amine, 3-n-propylcyclohexylamine, 4-n-propylcyclohexylamine, 2-i-propylcyclohexylamine, 3-i-propylcyclohexylamine, 4-i-propylcyclohexylamine, 2-n-butylcyclohexylamine, 3-n-butylcyclohexylamine, 4-n-butylcyclohexylamine, 2-t-butylcyclohexylamine, 3-t-butylcyclohexylamine, 4-t-butylcyclohexylamine, 2,3-dimethylcyclohexylamine, 2,4-dimethylcyclohexylamine, 2,5-dimethylcyclohexylamine, 2,6-dimethylcyclohexylamine, 3,4-dimethylcyclohexylamine, etc. Of these, cyclohexylamine, 2-methylcyclohexylamine, and 4-methylcyclohexylamine are particularly preferable. These alkyl-substituted cyclohexylamines may be used in the form of stereoisomer mixtures, with no particular restrictions.

These alkyl-substituted cyclohexylamines can be used singly or in combinations of two or more. Therefore, in the Specification and Claims herein, the three carbamoyl groups in General Formula (3) may be the same or different.

[Preferable Tricarboxylic Acid Tris(Alkyl-Substituted Cyclohexylamides)]

Preferable examples of the tricarboxylic acid tris(alkyl-substituted cyclohexylamide) to be prepared by the process of the present invention from a saturated aliphatic tricarboxylic acid, a saturated alicyclic tricarboxylic acid, or an aromatic tricarboxylic acid, and an alkyl-substituted cyclohexylamine include 1,2,3-propanetricarboxylic acid tris(cyclohexylamide), 1,2,3-propanetricarboxylic acid tris(2-methylcyclohexylamide), 1,2,3-propanetricarboxylic acid tris(4-methylcyclohexylamide), 1,3,5-cyclohexanetricarboxylic acid tris(cyclohexylamide), 1,3,5-cyclohexanetricarboxylic acid tris(2-methylcyclohexylamide), 1,3,5-cyclohexanetricarboxylic acid tris(4-methylcyclohexylamide), trimesic acid tris(cyclohexylamide), trimesic acid tris(2-methylcyclohexylamide), trimesic acid tris(4-methylcyclohexylamide), etc.

Of these, 1,2,3-propanetricarboxylic acid tris(cyclohexylamide), 1,2,3-propanetricarboxylic acid tris(2-methylcyclohexylamide), 1,3,5-cyclohexanetricarboxylic acid tris(cyclohexylamide), 1,3,5-cyclohexanetricarboxylic acid tris(2-methylcyclohexylamide), trimesic acid tris(cyclohexylamide), or trimesic acid tris(2-methylcyclohexylamide) is preferred when industrial usefulness is taken into account.

Of these, 1,2,3-propanetricarboxylic acid tris(2-methylcyclohexylamide) and trimesic acid tris(cyclohexylamide) are more preferable, and 1,2,3-propanetricarboxylic acid tris(2-methylcyclohexylamide) are especially preferable.

[Process for Producing Tricarboxylic Acid Tris(Alkyl-Substituted Cyclohexylamide)]

<Amidation Step>

According to the process of the present invention for producing a tricarboxylic acid tris(alkyl-substituted cyclohexylamide), the desired tricarboxylic acid tris(alkyl-substituted cyclohexylamide) can be easily produced, for example, merely by adding a boric acid compound and a phenol compound, or a boric acid ester of a boric acid compound and a phenol compound, prepared in advance by a conventional process, to a mixture of a tricarboxylic acid and an alkyl-substituted cyclohexylamine, and heating the mixture, either in the presence or absence of an azeotropic dehydration solvent. In particular, the order in which the tricarboxylic acid, alkyl-substituted cyclohexylamine, and boric acid compound, phenol compound or boric acid ester and azeotropic dehydration solvent are added does not affect the reaction, and may be suitably selected in view of ease of operation.

The above-mentioned alkyl-substituted cyclohexylamine is a reaction substrate, but is also believed to function as a reaction solvent. Also, the above-mentioned phenol compound is a constituent component of a catalyst, but is also believed to function as a reaction solvent.

The effect of thus using a boric acid compound and a phenol compound, or a boric acid ester of a boric acid compound and a phenol compound, as a dehydration condensation catalyst is that the formation of imide rings is suppressed and the yield of tricarboxylic acid tris(alkyl-substituted cyclohexylamide) is markedly increased, compared with the use of a boric acid compound alone.

The heating temperature during the reaction with the present invention is preferably 98 to 180° C., and more preferably 120 to 160° C. The temperature is preferably at least 100° C. so as to remove any water that is produced by the reaction, and the higher the heating temperature is, the more the reaction is accelerated, but a range of 120 to 160° C. is preferable to suppress side reactions. A temperature at which reflux continuously occurs in the reaction system is usually preferred.

With the present invention, the reaction can usually be conducted at atmospheric pressure, but the reaction system may also be put under reduced pressure to promote the removal of water from the reaction mixture. There are no particular restrictions on the reaction atmosphere, but the reaction is preferably conducted in the presence of an inert gas such as nitrogen or argon, or under an inert gas flow.

The reaction time is preferably from 0.1 to 50 hours, and more preferably 1 to 30 hours.

An azeotropic dehydration solvent may or may not be used in the present invention, but the use thereof is preferable from the standpoint of accelerating the reaction. Preferable azeotropic dehydration solvents are saturated aliphatic hydrocarbons, saturated alicyclic hydrocarbons, and aromatic hydrocarbons with a boiling point (the boiling point at 1 atm; the same applies hereinafter) of 98 to 180° C.

Specific examples include compounds such as heptane, iso-octane, methylcyclohexane, ethylcyclohexane, dimethylcyclohexane, trimethylcyclohexane, cycloheptane, toluene, ethylbenzene, n-propylbenzene, isopropylbenzene, p-xylene, p-cymene, mesitylene, n-octane, n-nonane and n-decane, and mixtures thereof, having a boiling point of between 98 and 180° C. Of these, dimethylcyclohexane, ethylcyclohexane, trimethylcyclohexane, ethylbenzene, n-propylbenzene, n-octane and n-nonane, and mixtures thereof, having a boiling point of between 120 and 160° C., are preferable in terms of suppressing side reactions. Xylene or an azeotropic dehydration solvent mixture obtained by suitably mixing these solvents so that the boiling point is from 130 to 150° C. is particularly preferable.

When the azeotropic dehydration solvents are used, there are no particular restrictions on the amount to be used, but the amount is usually from 500 to 5000 weight parts, and preferably from 800 to 2500 weight parts, per 100 weight parts of a tricarboxylic acid.

The proportion of an alkyl-substituted cyclohexylamine to a tricarboxylic acid in the present invention is preferably 3 to 50 moles, and more preferably 3 to 10 moles, and even more preferably 3 to 6 moles, of an alkyl-substituted cyclohexylamine per mole of a tricarboxylic acid. Any excess alkyl-substituted cyclohexylamine used can be separated from the desired product produced in the reaction, and then reused.

The boric acid compound that is used as a catalyst in the present invention can be any boric acid compound, and particularly an inorganic boric acid compound, capable of forming a boric acid ester with a phenol compound. Specific examples include orthoboric acid, metaboric acid, pyroboric acid, tetraboric acid, diboron trioxide, etc. Of these, orthoboric acid and diboron trioxide are preferable, and orthoboric acid is particularly preferable because it readily dissolves in the purification solvent used in the purification step discussed below, and can be easily separated from the desired product. These compounds can be used singly or as mixtures of two or more types.

There are no particular restrictions on the amount of the boric acid compound used, but it is usually 0.1 to 10 moles, and preferably 0.5 to 5 moles, per mole of tricarboxylic acid. The reaction promotion effect will tend to be inadequate if the amount is less than 0.1 moles, whereas even if more than 10 moles is used, the reaction promotion effect will tend not to improve in proportion to the amount used.

There are no particular restrictions on the phenol compound, so long as it can form a boric acid ester with the above-mentioned boric acid compound, but it is generally preferable to use benzene having one or two, preferably one, hydroxy groups, and optionally having one to three, preferably one to two, substituents. Examples of these substituents include $C_1$ to $C_3$ alkyl groups, specific examples of which include methyl, ethyl, and isopropyl.

Specific examples of phenol compounds include phenol, m-cresol, o-cresol, p-cresol, p-methoxyphenol, xylenol, catechol, etc. These can be used singly or as mixtures of two or more. Of these, phenol and cresol are particularly preferable.

There are no particular restrictions on the amount of the phenol compound used, but the amount is usually 0.5 to 20 moles, and preferably 1.0 to 10 moles, per mole of tricarboxylic acid. The reaction promotion effect will tend to be inadequate if the amount is less than 0.5 moles, whereas even if more than 20 moles is used, the reaction promotion effect will tend not to improve in proportion to the amount used.

Examples of a boric acid ester of a boric acid compound and a phenol compound include boric acid esters of the above-mentioned boric acid compounds and the above-mentioned phenol compounds, of which a boric acid ester of a boric acid compound and cresol is particularly preferable. The boric acid esters can be easily prepared by subjecting a boric acid compound and a phenol compound to dehydration condensation by a conventional process in the presence of an azeotropic dehydration solvent (see Example 4 below). As such azeotropic dehydration solvent, any of those listed in regard to the amidation reaction can be used.

There are no particular restrictions on the amount of the boric acid ester used, but the amount is usually 0.1 to 10 moles, and preferably 0.5 to 5 moles, per mole of tricarboxylic acid. The reaction promotion effect will tend to be inadequate if the amount is less than 0.1 moles, whereas even if more than 10 moles is used, the reaction promotion effect will tend not to improve in proportion to the amount used.

As the above-mentioned reaction of the present invention proceeds, the tricarboxylic acid tris(alkyl-substituted cyclohexylamide) produced precipitates as a solid from the reaction mixture.

The method for recovering the desired tricarboxylic acid tris(alkyl-substituted cyclohexylamide) upon completion of the reaction can be suitably selected. For instance, the desired product in the form of a solid that precipitates from the reaction mixture upon completion of the amidation reaction can be isolated by a conventional process such as filtration or centrifugation.

The reaction of the present invention affords a high conversion of the raw material tricarboxylic acid, and also a satisfactory yield of crude tricarboxylic acid tris(alkyl-substituted cyclohexylamide). In particular, using a mixture of a boric acid compound and a phenol compound, or a boric acid ester of phenol, according to the present invention suppresses imide ring formation and remarkably increases the yield of tricarboxylic acid tris(alkyl-substituted cyclohexylamide), compared to the case in which a boric acid compound is used alone.

Meanwhile, the reaction mother liquor obtained by filtering the desired product (crude tricarboxylic acid tris(alkyl-substituted cyclohexylamide)) can be subjected to an amidation reaction again as needed by adding a tricarboxylic acid, an alkyl-substituted cyclohexylamine, and an azeotropic dehydration solvent.

<Purification Step>

The solid thus obtained, namely, the crude tricarboxylic acid tris(alkyl-substituted cyclohexylamide), contains the amide-Imide represented by the above-mentioned General Formula (4), the boric acid compound and phenol compound, or the boric acid ester of a phenol compound, used as a catalyst, amine salts, and so forth as impurities.

Since these impurities include both organic and inorganic substances, removal of the impurities was considered either difficult or time-consuming with an ordinary purification process such as recrystallization. Research conducted by the inventors, however, has led to the surprising finding that these impurities can all be removed at once, and a high-purity tricarboxylic acid tris(alkyl-substituted cyclohexylamide) can be produced, by a simple process involving just washing with a solvent.

Therefore, the present invention provides a process for producing a purified tricarboxylic acid tris(alkyl-substituted cyclohexylamide), which comprises the step of washing the above-mentioned crude tricarboxylic acid tris(alkyl-substituted cyclohexylamide) with a solvent.

There are no particular restrictions on the solvent to be used in the above purification, so long as it is capable of dissolving the above-mentioned impurities contained in the crude tricarboxylic acid tris(alkyl-substituted cyclohexylamide).

The above-mentioned purification solvent is preferably methanol, ethanol, isopropanol, or like $C_1$ to $C_3$ lower aliphatic alcohol, or a mixture of these alcohols, or a mixed solvent of water and a $C_1$ to $C_3$ lower aliphatic alcohol, with methanol and ethanol being particularly preferable. When a mixed solvent of water and a lower aliphatic alcohol is used, the ratio of water to lower alcohol can be suitably selected from a wide range. Generally, the ratio of water:lower alcohol is preferably about 9:1 to 1:9, particularly about 5:5 to 1:9.

There are no particular restrictions on the amount of the lower alcohol used, but the lower alcohol is preferably used in an amount of 200 to 5000 weight parts per 100 weight parts of crude tricarboxylic acid tris(alkyl-substituted cyclohexylamide). This allows any byproducts and boric acid compound or boric acid ester, amine salts, etc., in the desired product to be removed with ease.

When a mixture of water and a lower alcohol is used, there are no particular restrictions on the amounts of such a mixture, but the mixture is preferably used in an amount of 200 to 5000 weight parts per 100 weight parts of crude tricarboxylic acid tris(alkyl-substituted cyclohexylamide).

Examples of washing method include a method in which the filtered desired product (crude tricarboxylic acid tris (alkyl-substituted cyclohexylamide)) is dispersed in a purification solvent and stirred and mixed at a temperature between room temperature and the boiling point of the purification solvent (generally from room temperature to about 100° C., and preferably from room temperature to about 90° C., and more preferably from room temperature to about 80° C.); and a method in which a solid of the desired product is showered with a purification solvent. These methods can also be suitably combined. The desired tricarboxylic acid tris(alkyl-substituted cyclohexylamide) can be easily obtained in a high purity by subjecting the washed solid to operations that are normally carried out, such as filtration and reduced-pressure drying.

The extent of the purification in the above-mentioned purification step can be suitably selected according to the type and amount of purification solvent used, the washing duration, the washing temperature, and so forth. From an industrial standpoint, it is preferable if the boron content measured by subjecting the tricarboxylic acid tris(alkyl-substituted cyclohexylamide) thus obtained to ICP spectrometry (inductively coupled plasma atomic emission spectrometry) is 100 ppm or less, and more preferably 50 ppm or less, and even more preferably 20 ppm or less

EXAMPLES

The present invention will now be described in further detail by giving Examples, but the present invention is not limited whatsoever by these examples. The starting substances used here are either known compounds or compounds that can be produced by a known process.

In the following discussion, the "yield" is the yield based on the raw material tricarboxylic acid. It has been confirmed from FT-IR that the raw material tricarboxylic acid forms an amine salt that is a reaction intermediate with 2-methylcyclohexylamine, and the conversion thereof is 100%. Since the desired product that is obtained is substantially insoluble under the following reaction conditions, the yield is substantially equal to the selectivity.

The GC purity, melting point, infrared absorption spectrometry, organic elemental analysis, and boron content were measured by the following methods.

1) GC (Gas Chromatography) Purity (%)

Apparatus: GC-17A made by Shimadzu Corporation

Column: DB-1HT 0.25 mm i.d.×30 m (film thickness of 0.1 μm), made by J&W Scientific Column temperature: initial temperature of 250° C. (holding time of 5 minutes)→10° C./min→300° C.→20° C./min→380° C. (holding time of 15 minutes)

Carrier gas: helium, 150 kPa

Split ratio: 1/30

Detector: FID

Injection temperature: 350° C.

Detector temperature: 380° C.

2) Melting Point (° C.)

The melting point was measured under the following conditions using a differential scanning calorimeter (trade name "DSC-50," made by Shimadzu Corporation), and was the peak top temperature of the maximum endothermic peak. However, if the endothermic peak was not measured at 400° C. or below, the melting point was assumed to be 400° C. or higher.

Nitrogen flow: 30 ml/minute

Temperature elevation rate: 10° C./minute

Sample weight: 5 mg

Standard sample: silica gel, 5 mg

3) Infrared Absorption Measurement Method

This was measured by ATR (attenuated total reflectance) process using an FT-IR apparatus (trade name "Spectrum One," made by Perkin-Elmer).

4) Elemental Analysis

This was conducted using a model EA1110 made by CE Instruments.

5) Boron Content

This was measured using an ICP spectrometer (trade name "Optima 2000 DV," made by Perkin-Elmer).

Example 1

(a) Amidation Reaction Step 3.52 g (20 mmol) of 1,2,3-propanetricarboxylic acid (made by Nacalai Tesque), 13.6 g (120 mmol) of 2-methylcyclohexylamine, 6.5 g (60 mmol) of cresol (made by Nacalai Tesque), 0.5 g (7.2 mmol) of diboron trioxide, and 80 g of xylene were supplied to a 200 mL four-necked flask equipped with a mechanical stirrer, a thermometer, and a water separator with an attached reflux condenser tube. The mixture was heated at the reflux temperature of the azeotropic solvent for 3 hours under a nitrogen atmosphere, and an amidation reaction was conducted while the water that was formed was continuously removed azeotropically. Upon completion of the reaction, the precipitated solid was filtered under reduced pressure, which gave crude 1,2,3-propanetricarboxylic acid tris(2-methylcyclohexylamide) as a white solid.

(b) Purification Step

The white solid thus obtained was stirred and washed for 1 hour at room temperature in 100 mL of methanol, and the mixture was then filtered, and the solid was dried under reduced pressure for 2 hours at 120° C., which gave 4.61 g (49.9% yield) of purified 1,2,3-propanetricarboxylic acid tris(2-methylcyclohexylamide). The white solid thus obtained had a GC purity of 99.7%, and it was confirmed by the following measurement to have the structure of the desired product.

FT-IR (ATR method): 1643, 1542, 3302 cm$^{-1}$
Elemental analysis:
Measured values: C, 70.44; H, 10.22; N, 9.13.
Calculated values: C, 70.22; H, 10.27; N, 9.11.
Melting point: 320° C.
Boron content: 15 ppm

Example 2

The reaction and purification were carried out in the same manner as in Example 1 except that 13 g (120 mmol) of cresol and 1.0 g (14.2 mmol) of diboron trioxide were used in place of 6.5 g (60 mmol) of cresol and 0.5 g (7.2 mmol) of diboron trioxide, which gave 5.80 g (62.8% yield) of 1,2,3-propanetricarboxylic acid tris(2-methylcyclohexylamide) as a white solid. The white solid thus obtained had a GC purity of 99.7% and a boron content of 18 ppm.

Example 3

A reaction was conducted in the same manner as in step (a) of Example 1 except that 5.1 g (60 mol) of phenol was used in place of 6.5 g (60 nmol) of cresol.

Upon completion of the reaction, purification was conducted in the same manner as in step (b) of Example 1, which gave 4.70 g (50.9% yield) of 1,2,3-propanetricarboxylic acid tris(2-methylcyclohexylamide). The white solid thus obtained had a GC purity of 99.5% and a boron content of 25 ppm.

Example 4

(a) Production of Boric Acid Ester 13.6 g (120 mmol) of cresol, 1.0 g (14 mm=1) of diboron trioxide, and 80 g of xylene were supplied to the same apparatus as described in Example 1, the contents were refluxed under heating for 1 hour under a nitrogen atmosphere, and the water that was produced was continuously removed azeotropically, which gave a xylene solution of a tricresol boric acid ester.

(b) Amidation Reaction

Next, 3.52 g (20 mmol) of 1,2,3-propanetricarboxylic acid (made by Nacalai Tesque) and 13.6 g (120 mmol) of 2-methylcyclohexylamine were added to the xylene solution of a tricresol boric acid ester obtained above, and the contents were refluxed under heating and reacted for 3 hours. This gave a crude 1,2,3-propanetricarboxylic acid tris(2-methylcyclohexylamide) as a white solid.

(c) Purification Step

Upon completion of the amidation reaction, the product was purified in the same manner as in Example 1, which gave 6.2 g (67.1% yield) of 1,2,3-propanetricarboxylic acid tris(2-methylcyclohexylamide). The white solid thus obtained had a GC purity of 99.6% and a boron content of 3 ppm.

Example 5

The production of boric acid ester, amidation reaction and purification were carried out in the same manner as in Example 4 except that 1.0 g (16 mmol) of orthoboric acid was used in place of 1.0 g (14 mmol) of diboron trioxide, which gave 5.82 g (63.0% yield) of 1,2,3-propanetricarboxylic acid tris(2-methylcyclohexylamide). The white solid thus obtained had a GC purity of 99.5% and a boron content of 5 ppm.

Example 6

The production of boric acid ester, amidation reaction and purification were carried out in the same manner as in Example 4 except that 11.9 g (120 nmol) of cyclohexylamine and 1.0 g (16 mmol) of orthoboric acid were used in place of 13.6 g (120 mmol) of 2-methylcyclohexylamine and 1.0 g (14 mmol) of diboron trioxide, which gave 5.63 g (67.2% yield) of 1,2,3-propanetricarboxylic acid tris(cyclohexylamide) as a white solid. The white solid thus obtained had a GC purity of 99.4%, and it was confirmed by the following measurement to have the structure of the desired product.

FT-IR (ATR method): 1631, 1544, 3287 cm$^{-1}$
Elemental analysis:
Measured values: C, 68.70; H, 10.52; N, 9.98.
Calculated values: C, 68.68; H, 10.86; N, 10.06.
Melting point: 308° C.
Boron content: 4 ppm

Example 7

The production of boric acid ester, amidation reaction and purification were carried out in the same manner as in Example 4 except that 4.20 g (20 mmol) of trimesic acid and 1.0 g (16 mmol) of orthoboric acid were used in place of 3.52 g (20 mmol) of 1,2,3-propanetricarboxylic acid and 1.0 g (14 mmol) of diboron trioxide, and the amidation reaction time was changed to 6.5 hours, which gave 7.87 g (79.5% yield) of trimesic acid tris(2-methylcyclohexylamide) as a white solid.

FT-IR (ATR method): 3221, 3059, 1631, 1552 cm$^{-1}$
Elemental analysis:
Measured values: C, 72.58; H, 9.35; N, 8.62.
Calculated values: C, 72.67; H, 9.16; N, 8.48.
Melting point: 400° C. or higher Example 8

The production of boric acid ester, amidation reaction and purification were carried out in the same manner as in Example 4 except that 4.20 g (20 mmol) of trimesic acid, 17.8 g (180 mmol) of cyclohexylamine, and 1.0 g (16 mmol) of orthoboric acid were used in place of 3.52 g (20 mmol) of 1,2,3-propanetricarboxylic acid, 13.6 g (120 mmol) of 2-methylcyclohexylamine, and 1.0 g (14 mmol) of diboron trioxide, and the amidation reaction time was changed to 8 hours, which gave 7.18 g (79.2% yield) of trimesic acid tris(cyclohexylamide) as a white solid.
FT-IR (ATR method): 3213, 3052, 1629, 1555 cm$^{-1}$
Elemental analysis:
Measured values: C, 71.58; H, 8.46; N, 9.34.
Calculated values: C, 71.47; H, 8.67; N, 9.27.
Melting point: 360° C.

Example 9

The production of boric acid ester, amidation reaction and purification were carried out in the same manner as in Example 4 except that 4.32 g (20 mmol) of 1,3,5-cyclohexanetricarboxylic acid and 1.0 g (16 mmol) of orthoboric acid were used in place of 3.52 g (20 mmol) of 1,2,3-propanetricarboxylic acid and 1.0 g (14 mmol) of diboron trioxide, which gave 8.02 g (80.3% yield) of 1,3,5-cyclohexanetricarboxylic acid tris(2-methylcyclohexylamide) as a white solid.
FT-IR (ATR method): 3287, 1638, 1542 cm$^{-1}$
Elemental analysis:
Measured values: C, 71.92; H, 10.46; N, 8.34.
Calculated values: C, 71.80; H, 10.25; N, 8.38.
Melting point: 400° C. or higher Example 10

The production of boric acid ester, amidation reaction and purification were carried out in the same manner as in Example 4 except that 4.32 g (20 mmol) of 1,3,5-cyclohexanetricarboxylic acid, 11.9 g (120 mmol) of cyclohexylamine, and 1.0 g (16 mmol) of orthoboric acid were used in place of 3.52 g (20 mmol) of 1,2,3-propanetricarboxylic acid, 13.6 g (120 mmol) of 2-methylcyclohexylamine, and 1.0 g (14 mmol) of diboron trioxide, and the reaction time was changed to 6 hours, which gave 8.14 g (88.7% yield) of 1,3,5-cyclohexanetricarboxylic acid tris(cyclohexylamide) as a white solid.
FT-IR (ATR method): 3284, 1637, 1545 cm$^{-1}$
Elemental analysis:
Measured values: C, 70.74; H, 10.10; N, 9.20.
Calculated values: C, 70.53; H, 9.87; N, 9.15.
Melting point: 400° C. or higher Comparative Example 1

The reaction and purification were carried out in the same manner as in Example 1 except that 6.5 g (60 mmol) of cresol was not used, which gave 1.90 g (20.6% yield) of purified 1,2,3-propanetricarboxylic acid tris(2-methylcyclohexylamide). The reaction mother liquor or a concentrate thereof was subjected to GC-MS analysis and FT-IR analysis, which confirmed the presence of an amide-imide as a reaction byproduct.

Comparative Example 2

The reaction and purification were carried out in the same manner as in Example 1 except that 1.0 g (14.2 mmol) of diboron trioxide was not used, but the desired 1,2,3-propanetricarboxylic acid tris(2-methylcyclohexylamide) was not obtained.

Comparative Example 3

The reaction and purification were carried out in the same manner as in Example 2 except that 15.6 g (120 mmol) of 2-ethylhexanol was used in place of 13 g (120 mmol) of cresol, which gave 0.17 g (1.8% yield) of purified 1,2,3-propanetricarboxylic acid tris(2-methylcyclohexylamide).

INDUSTRIAL APPLICABILITY

Up to now, production of a tricarboxylic acid tris(alkyl-substituted cyclohexylamide) entailed a complicated process, or necessitated costly reaction agents that produced large quantities of phosphorus-containing waste. With the production process and purification process of the present invention, however, a tricarboxylic acid tris(alkyl-substituted cyclohexylamide) can be produced by an industrially simple process at a high purity and yield, and at high productivity, which is industrially advantageous.

This tricarboxylic acid tris(alkyl-substituted cyclohexylamide) exhibits excellent thermal stability, and acts as a clarifier for polypropylene-based resins to thereby impart excellent transparency.

The invention claimed is:
1. A process for producing a tricarboxylic acid tris(alkyl-substituted cyclohexylamide) represented by General Formula (3):

[Chemical formula 1]

$$R^1\left(CONH-\underset{R^3}{\overset{R^2}{\bigcirc}}\right)_3 \quad (3)$$

wherein $R^1$ is a $C_3$ to $C_{10}$ trivalent saturated aliphatic hydrocarbon group, a $C_5$ to $C_{15}$ trivalent saturated alicyclic hydrocarbon group, or a $C_6$ to $C_{15}$ trivalent aromatic hydrocarbon group, and $R^2$ and $R^3$ are the same or different and are each a hydrogen atom or a $C_1$ to $C_4$ linear or branched alkyl group,
the process comprising the step of subjecting a tricarboxylic acid represented by the following General Formula (1):

[Chemical formula 2]

$$R^1(COOH)_3 \quad (1)$$

wherein $R^1$ has the same meaning as $R^1$ in General Formula (3), and an alkyl-substituted cyclohexylamine represented by the following General Formula (2):

[Chemical formula 3]

$$\underset{R^3}{\overset{R^2}{\bigcirc}}-NH_2 \quad (2)$$

wherein $R^2$ and $R^3$ have the same meanings as $R^2$ and $R^3$ in General Formula (3) to an amidation reaction
  (a) in the presence of a boric acid compound and a phenol compound, or (b) in the presence of a boric acid ester obtained by the dehydration condensation of a boric acid compound and a phenol compound, to obtain a crude tricarboxylic acid tris(alkyl-substituted cyclohexylamide).

2. The process according to claim 1, wherein the boric acid compound is at least one member selected from the group consisting of orthoboric acid, metaboric acid, pyroboric acid, tetraboric acid and diboron trioxide.

3. The process according to claim 1, wherein the phenol compound is phenol or cresol.

4. The process according to claim 1, wherein the boric acid ester is a boric acid ester formed from phenol or cresol and at least one boric acid compound selected from the group consisting of orthoboric acid, metaboric acid, pyroboric acid, tetraboric acid and diboron trioxide.

5. The process according to claim 1, wherein the amidation reaction is conducted at a reaction temperature of 98 to 180° C.

6. The process according to claim 1, wherein the amidation reaction is conducted in the presence of an azeotropic dehydration solvent.

7. The process according to claim 6, wherein the azeotropic dehydration solvent is a saturated aliphatic hydrocarbon, a saturated alicyclic hydrocarbon, an aromatic hydrocarbon, or a mixture of these.

8. The process according to claim 7, wherein the azeotropic dehydration solvent has a boiling point of 120 to 160° C.

9. The process according to claim 1, wherein the tricarboxylic acid tris(alkyl-substituted cyclohexylamide) is 1,2,3-propanetricarboxylic acid tris(cyclohexylamide), 1,2,3-propanetricarboxylic acid tris(2-methylcyclohexylamide), trimesic acid tris(cyclohexylamide), trimesic acid tris(2-methylcyclohexylamide), 1,3,5-cyclohexanetricarboxylic acid tris(cyclohexylamide), or 1,3,5-cyclohexanetricarboxylic acid tris(2-methylcyclohexylamide).

10. The process according to claim 9, wherein the tricarboxylic acid tris(alkyl-substituted cyclohexylamide) is 1,2,3-propanetricarboxylic acid tris(2-methylcyclohexylamide).

11. The process according to claim 1, which further comprises the step of purifying the crude tricarboxylic acid tris(alkyl-substituted cyclohexylamide).

12. The process according to claim 11, wherein the purification step comprises the step of washing the crude tricarboxylic acid tris(alkyl-substituted cyclohexylamide) with a $C_1$ to $C_3$ aliphatic alcohol or with a mixture of water and a $C_1$ to $C_3$ aliphatic alcohol.

13. The process according to claim 12, wherein the purification step is conducted until the boron content in the tricarboxylic acid tris(alkyl-substituted cyclohexylamide) as measured by ICP spectrometry reaches 100 ppm or less.

* * * * *